(12) United States Patent
Kozawa

(10) Patent No.: US 10,596,034 B2
(45) Date of Patent: Mar. 24, 2020

(54) CRUSHING TIP FOR EYE SURGERY

(71) Applicant: Tadahiko Kozawa, Mito (JP)

(72) Inventor: Tadahiko Kozawa, Mito (JP)

( * ) Notice: Subject to any disclaimer, the term of this patent is extended or adjusted under 35 U.S.C. 154(b) by 101 days.

(21) Appl. No.: 15/661,746

(22) Filed: Jul. 27, 2017

(65) Prior Publication Data
US 2018/0028360 A1   Feb. 1, 2018

(30) Foreign Application Priority Data

Jul. 27, 2016 (JP) .................... 2016-146845

(51) Int. Cl.
*A61F 9/007* (2006.01)
*A61M 1/00* (2006.01)

(52) U.S. Cl.
CPC ......... *A61F 9/00745* (2013.01); *A61M 1/008* (2013.01); *A61M 2210/0612* (2013.01)

(58) Field of Classification Search
CPC ..... A61F 9/00745; A61B 2017/320072; A61B 17/320068; A61M 1/008; A61M 25/0026
See application file for complete search history.

(56) References Cited

U.S. PATENT DOCUMENTS

| 5,487,747 | A |   | 1/1996 | Stagmann et al. |
| 5,569,182 | A | * | 10/1996 | Twardowski ....... A61M 5/1582 604/264 |
| 5,693,062 | A |   | 12/1997 | Stegmann et al. |
| 5,725,495 | A | * | 3/1998 | Strukel ............... A61M 1/0043 604/22 |
| 6,126,629 | A |   | 10/2000 | Perkins et al. |
| 2004/0267211 | A1 |   | 12/2004 | Akahoshi |
| 2006/0100653 | A1 | * | 5/2006 | Akahoshi ............ A61F 9/00745 606/169 |

(Continued)

FOREIGN PATENT DOCUMENTS

| EP | 0623328 A1 | 11/1994 |
| JP | H05-070515 U | 9/1993 |
| JP | H07-000443 A | 1/1995 |

(Continued)

OTHER PUBLICATIONS

PCT/ISA/210, "International Search Report for International Application No. PCT/JP2017/026982," dated Sep. 5, 2017.

(Continued)

*Primary Examiner* — Diane D Yabut
*Assistant Examiner* — Majid Jamialahmadi
(74) *Attorney, Agent, or Firm* — Manabu Kankesaka

(57) ABSTRACT

A crushing tip dramatically increases a contact area between the crushing tip ultrasonic vibrated and a crystalline lens, compared to conventional crushing tips, and can efficiently crush and emulsify the crystalline lens. In the crushing tip, which is inserted into the crystalline lens of an eye of a patient at a time of an eye surgery for crushing, sucking, and discharging the crystalline lens by providing the ultrasonic vibrations, one or a plurality of partition walls is provided in such a way as to cross a through hole inside the through hole of a cylindrical tip main member. A tip of the partition wall may project from a tip of the tip main member, and a projecting portion may extend to an outer peripheral edge of the tip main member in a width direction as well.

7 Claims, 8 Drawing Sheets

(56) References Cited

U.S. PATENT DOCUMENTS

2009/0099536 A1  4/2009  Akahoshi

FOREIGN PATENT DOCUMENTS

| | | |
|---|---|---|
| JP | 2004-358227 A | 12/2004 |
| JP | 2009-095662 A | 5/2009 |
| JP | 4473192 B2 | 6/2010 |
| JP | 4800802 B2 | 10/2011 |
| WO | 2011/151837 A1 | 12/2011 |
| WO | 2013/125056 A1 | 8/2013 |

OTHER PUBLICATIONS

PCT/ISA/237, "Written Opinion of the International Searching Authority for International Application No. PCT/JP2017/026982," dated Sep. 5, 2017.

* cited by examiner

Fig. 7(a)
Fig. 7(b)
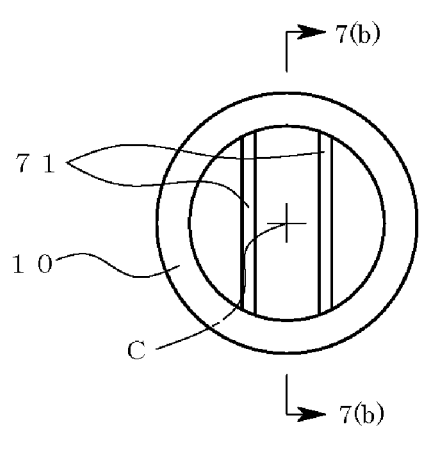
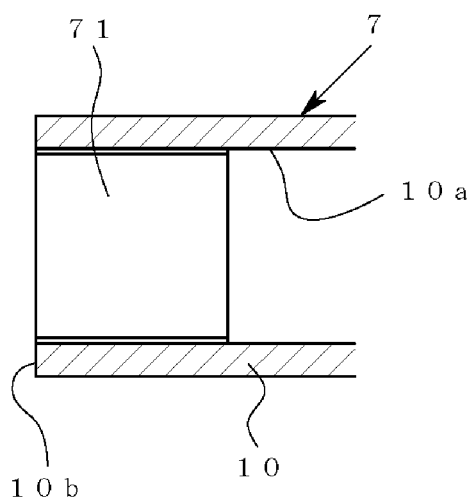
Fig. 8(a)
Fig. 8(b)
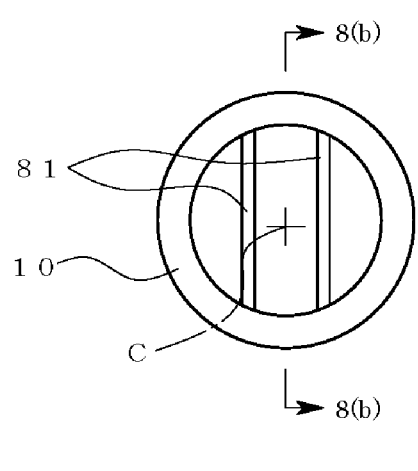
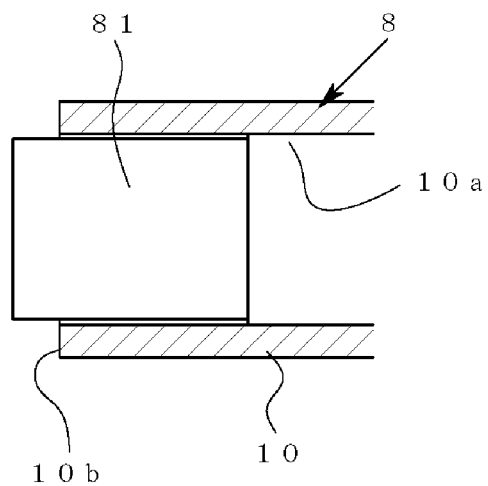

Fig. 9(a)
Fig. 9(b)
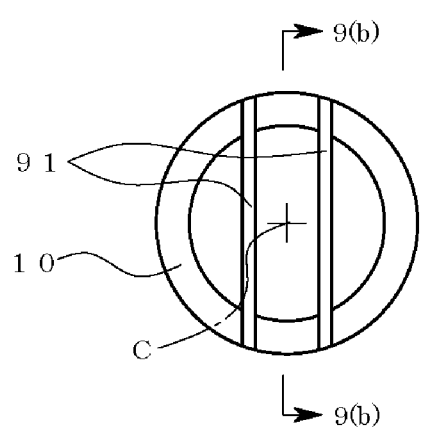
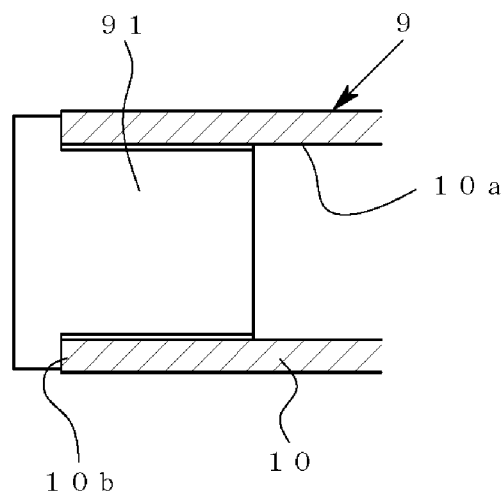
Fig. 10(a)
Fig. 10(b)
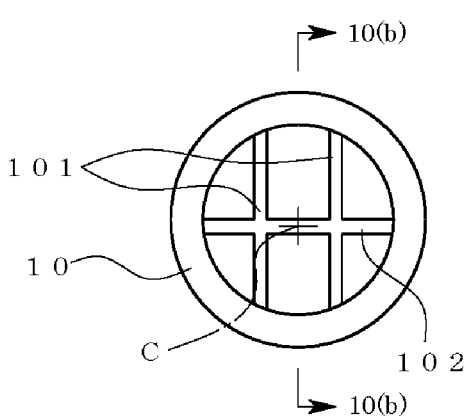
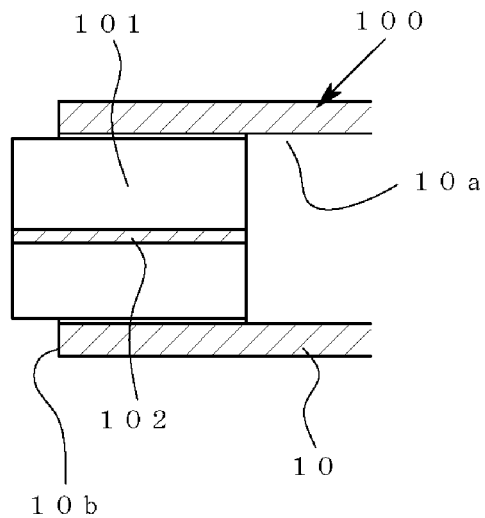

Fig. 13(a)  Fig. 13(b)  Fig. 13(c)
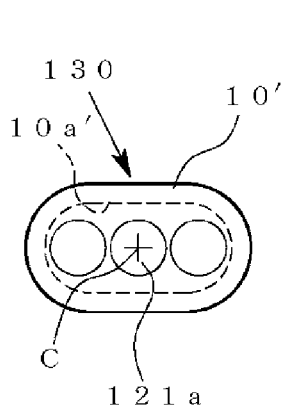
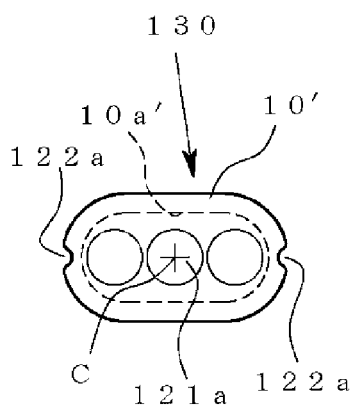
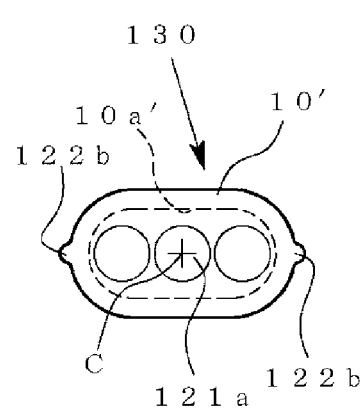
Fig. 14(a)  Fig. 14(b)
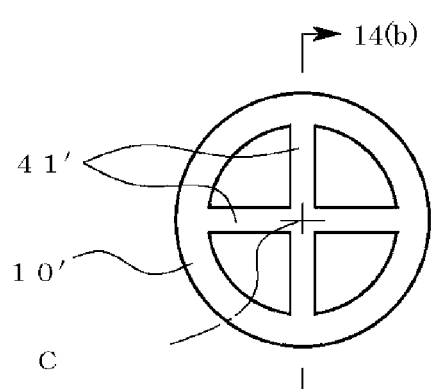
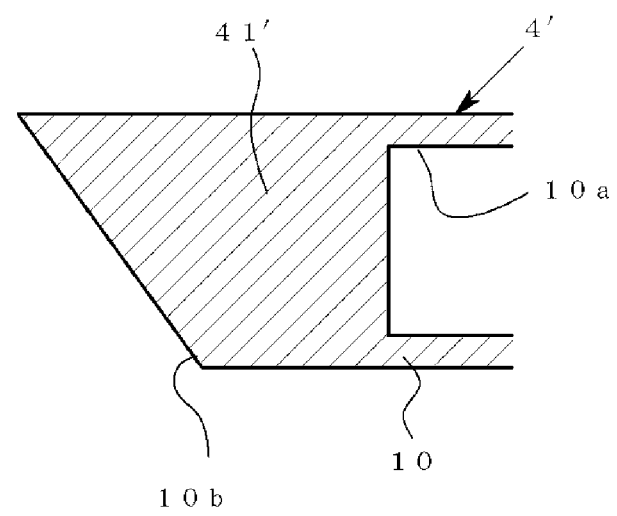

CRUSHING TIP FOR EYE SURGERY

BACKGROUND OF THE INVENTION AND RELATED ART STATEMENT

The present invention relates to a crushing tip used for an eye surgery using ultrasonic vibrations, and especially, relates to the crushing tip which crushes, sucks, and discharges a crystalline lens in the eye surgery for treating a cataract and the like.

For example, as for a method for operating the crystalline lens of an eye of a patient who has the cataract, recently, phacoemulsification and aspiration (PEA) is becoming widespread. In this operation, a crushing tip attached to a horn of an ultrasonic handpiece which generates ultrasonic vibrations is prepared, and the crushing tip is inserted into the crystalline lens to provide the ultrasonic vibrations, so that the crystalline lens is crushed and emulsified by the crushing tip, and after the emulsified crystalline lens is sucked and taken out by the crushing tip, a replacement artificial lens (intraocular lens) is implanted in a capsule of crystalline lens wherein an inside becomes empty so as to perform a vision correction (for example, see Japanese Unexamined Patent Application Publication No. 2009-95662 (see paragraph [0002]); WIPO Publication No. WO2013/125056 (see paragraph [0004]); US Patent Application Publication No. US2009/0099536A1; Japanese Patent No. 4800802; and Japanese Patent No. 4473192).

Incidentally, as for such a crushing tip, in order to enhance a crushing efficiency of the crystalline lens by a torsional mode (repetition rotational mode), there is used a crushing tip wherein a tip portion is curved (for example, see paragraph [0002] of Japanese Unexamined Patent Application Publication No. 2009-95662).

However, the crushing tip wherein the tip is curved as mentioned above has a disadvantage of easily generating a cavitation which has a possibility of causing a negative effect to an iris or an endothelial cell by swinging vibrations of the tip of the crushing tip (for example, see paragraph [0004] of WIPO Publication No. WO2013/125056). Also, since a center of gravity is located outside the tip, at a time of the torsional mode, a "shaft shift" occurs so as to increase an invasion into an incised wound, thereby there is a possibility of generating an "incised wound insufficiency". Moreover, since a current cataract surgery has a small incision, most cataract surgeries are performed "without a suture", however, if a large aggression is applied to the incised wound, self-closing does not occur, thereby having a problem of increasing burden on an operator and a patient. Moreover, in the crushing tip wherein the tip is curved, the tip faces downward, so that the tip of the crushing tip contacts a posterior capsule so as to have a possibility of a posterior capsule rupture as well.

In view of the aforementioned problems, recently, a crushing tip with a straight type wherein a whole crushing tip has a straight shape has become popular, however, in such a straight-type crushing tip, a problem is how the crystalline lens can be efficiently crushed and emulsified, and there are proposed various tips for enhancing a crushing and emulsifying efficiency while restraining the cavitation from occurring (see WIPO Publication No. WO2013/125056; US Patent Application Publication No. US2009/0099536A1; Japanese Patent No. 4800802; and Japanese Patent No. 4473192).

However, even in the crushing tips described in the aforementioned Patent Publications, there is a problem that the crushing and emulsifying efficiency is still insufficient.

The present invention is made in view of the aforementioned problem, and an object of the present invention is to provide a crushing tip which can largely improve the crushing and emulsifying efficiency relative to the conventional crushing tips, and especially, the crushing tip which can enhance the crushing and emulsifying efficiency while effectively restraining the cavitation from occurring.

Further objects and advantages of the invention will be apparent from the following description of the invention.

SUMMARY OF THE INVENTION

In the aforementioned conventional crushing tips, a cross-sectional shape of the crushing tip is devised, or a depression and a projection are provided mainly on an outside surface or inside a through hole of the crushing tip. On the other hand, the present invention is formed such that a partition wall crossing the through hole is provided inside the through hole of the crushing tip.

Specifically, in a first aspect, a crushing tip, which is inserted into a crystalline lens of an eye of a patient at a time of an eye surgery for crushing, sucking, and discharging the crystalline lens by providing ultrasonic vibrations, includes a cylindrical tip main member, and one or a plurality of partition walls in such a way as to cross a through hole of the tip main member. The partition wall crossing the through hole is provided inside the through hole, so that while dramatically increasing a contact area with the crystalline lens, a cavitation can be restrained from occurring as well. Also, even if the cavitation occurs around the partition wall, the cavitation occurs inside the through hole, and the crystalline lens which is crushed at the same time that the ultrasonic vibrations are provided is sucked, so that the cavitation which occurs inside the through hole does not diffuse to an outside of the crushing tip.

The crushing tip of the present invention can provide definite effects such as improving a crushing efficiency, restraining the cavitation from occurring, and the like even with a bend type wherein a tip is curved. However, in a second aspect, in the tip main member of the crushing tip, a straight type which is formed in a straight shape in a transmitting axial line direction of the ultrasonic vibrations is adopted so as to obtain a further greater effect. Especially, in a third aspect, in the tip main member, at least a portion to be inserted into the crystalline lens is formed in a circular shape or an oval shape in cross section so as to reduce the occurrence of the cavitation on an outer peripheral face of the crushing tip approximately down to zero.

As for the types wherein the partition wall is provided inside the through hole, there are various partition walls. For example, in a fourth aspect, a tip of the partition wall projects from a tip of the tip main member; in a fifth aspect, the tip of the partition wall projecting from the tip of the tip main member extends to an outer peripheral edge of the tip main member in a width direction; in a sixth aspect, the plurality of partition walls is intersected and provided; and in a seventh aspect, the plurality of partition walls is provided in parallel.

BRIEF DESCRIPTION OF THE DRAWINGS

FIG. 7(a) is an enlarged front view according to a seventh embodiment of the crushing tip of the present invention, and FIG. 7(b) is a cross-sectional view taken along a line 7(b)-7(b) in FIG. 7(a).

FIG. 8(a) is an enlarged front view according to an eighth embodiment of the crushing tip of the present invention, and FIG. 8(b) is a cross-sectional view taken along a line 8(b)-8(b) in FIG. 8(a).

FIG. 9(a) is an enlarged front view according to a ninth embodiment of the crushing tip of the present invention, and FIG. 9(b) is a cross-sectional view taken along a line 9(b)-9(b) in FIG. 9(a).

FIG. 10(a) is an enlarged front view according to a tenth embodiment of the crushing tip of the present invention, and FIG. 10(b) is a cross-sectional view taken along a line 10(b)-10(b) in FIG. 10(a).

FIGS. 13(a), 13(b), and 13(c) are enlarged front views according to still another embodiment of the crushing tip of the present invention.

FIG. 14(a) is an enlarged front view according to still another embodiment of the crushing tip of the present invention, and FIG. 14(b) is a cross-sectional view taken along a line 14(b)-14(b) in FIG. 14(a).

DETAILED DESCRIPTION OF PREFERRED EMBODIMENTS

Preferred embodiments of a crushing tip of the present invention will be explained in detail with reference to the drawings.

First Embodiment

Figure 1A:
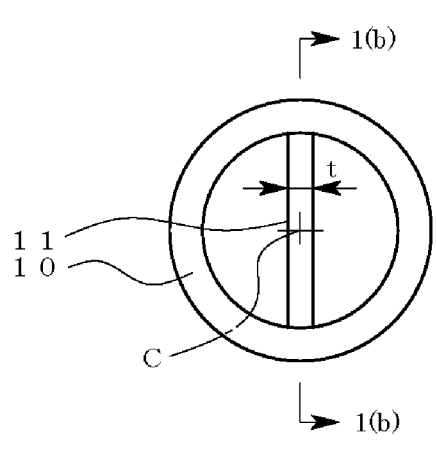
FIG. 1(a) is an enlarged front view according to a first embodiment of a crushing tip of the present invention.
Figure 1B:
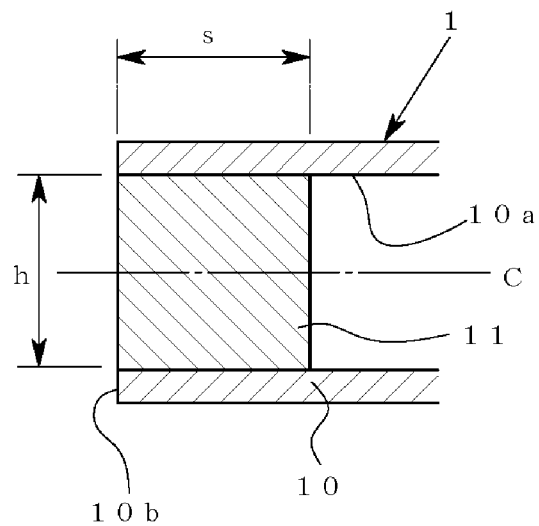
FIG. 1(b) is a cross-sectional view taken along a line 1(b)-1(b) in FIG. 1(a).

FIG. 1(a) is an enlarged front view according to a first embodiment of the crushing tip of the present invention, and FIG. 1(b) is a cross-sectional view taken along a line 1(b)-1(b) in FIG. 1(a).

A crushing tip 1 of the embodiment includes a tip main member 10 formed by a narrow tube such that it can be inserted into a crystalline lens of an eye; and a partition wall 11 provided inside a through hole 10a of the tip main member 10. In the tip main member 10, at least a portion to be inserted into the crystalline lens is formed in a cross-sectional circular shape so that a cavitation is difficult to occur when the tip main member 10 is inserted into the crystalline lens and ultrasonic vibrations are provided.

Also, preferably, the tip main member 10 is a straight type extending in a straight shape in a moving direction (rotational center C direction) of the ultrasonic vibrations generated from a horn of an ultrasonic handpiece (not shown in the drawings).

Incidentally, an outer diameter of the tip main member 10 is approximately from 0.8 mm to 1.5 mm, and an inner diameter thereof is approximately from 0.5 mm to 1.2 mm.

As shown in FIG. 1(a), the partition wall 11 is provided inside the through hole 10a in such a way as to cross the through hole 10a passing a rotational center C of the crushing tip 1, and one end thereof (a left end in FIG. 1(b)) is positioned inside the same face as a tip face 10b of the tip main member 10 as shown in FIG. 1(b). For example, the partition wall 11 can be integrally formed with the tip main member 10 by a laser micro processing method or a cutting processing method, and the partition wall 11 as a separate member can be welded to an inner peripheral face of the through hole 10a by the laser micro processing method. A depth s of the partition wall 11 is approximately the same as the outer diameter of the tip main member 10 as a standard, and a thickness t is approximately from 0.08 mm to 0.15 mm as the standard.

Second Embodiment

Figure 2A:
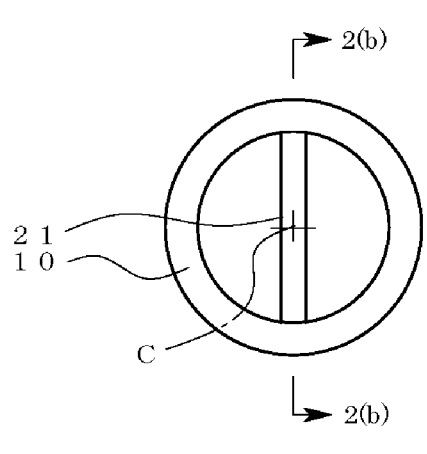
FIG. 2(a) is an enlarged front view according to a second embodiment of the crushing tip of the present invention.
Figure 2B:
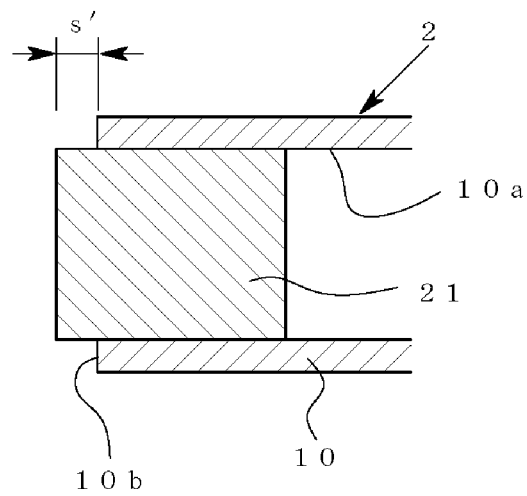
FIG. 2(b) is a cross-sectional view taken along a line 2(b)-2(b) in FIG. 2(a).

FIG. 2(a) is an enlarged front view according to a second embodiment of the crushing tip of the present invention, and FIG. 2(b) is a cross-sectional view taken along a line 2(b)-2(b) in FIG. 2(a). In the same portions and the same members as the embodiment in FIGS. 1(a) and 1(b), the same signs are assigned, and a detailed explanation is omitted (the same as other embodiments explained hereinafter).

A crushing tip 2 of the embodiment differs from the crushing tip 1 of the first embodiment in that as shown in FIG. 2(b), one end (left end in FIG. 2(b)) of a partition wall 21 projects from the tip face 10b of the tip main member 10 with the same width, as the partition wall 21 of the first embodiment. The width is h in a direction of crossing the through hole 10a in FIG. 1(b), and is the same as that in the embodiments hereinafter.

The aforementioned one end of the partition wall 21 is positioned parallel to the tip face 10b of the tip main member 10. Regarding a projecting amount s' of the partition wall 21, the outer diameter of the tip main member 10 is approximately from 0.8 mm to 1.5 mm, and if the projecting amount s' is too large, there is a possibility that the cavitation generated by the partition wall 21 is released to an outside without being completely sucked, so that the projecting amount s' of the partition wall 21 may be a degree which does not exceed the outer diameter of the tip main member 10 as the standard. Incidentally, the standard of the projecting amount s' is the same as that in the other embodiments explained hereinafter.

Third Embodiment

Figure 3A:
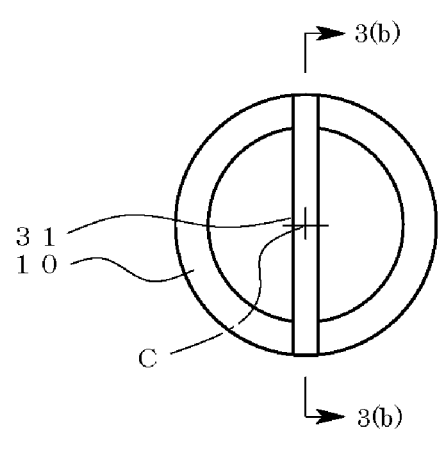
FIG. 3(a) is an enlarged front view according to a third embodiment of the crushing tip of the present invention.
Figure 3B:
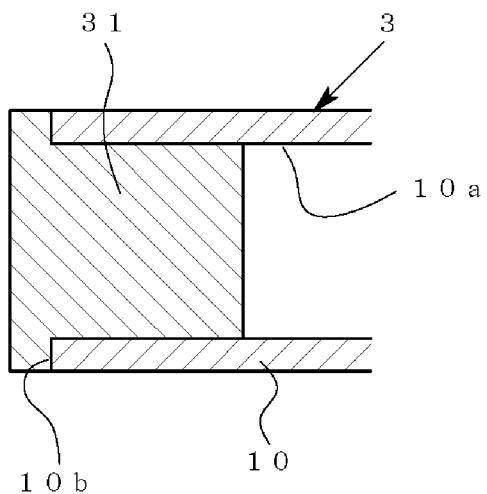
FIG. 3(b) is a cross-sectional view taken along a line 3(b)-3(b) in FIG. 3(a).

FIG. 3(a) is an enlarged front view according to a third embodiment of the crushing tip of the present invention, and FIG. 3(b) is a cross-sectional view taken along a line 3(b)-3(b) in FIG. 3(a).

A crushing tip 3 of the embodiment differs from the crushing tip 2 of the second embodiment in that as shown in FIGS. 3(a) and 3(b), one end (left end in FIG. 3(b)) of a partition wall 31 projecting from the tip face 10b of the tip main member 10 extends to an outer peripheral edge of the tip main member 10 in a width direction in FIG. 3(a).

Fourth Embodiment

Figure 4A:
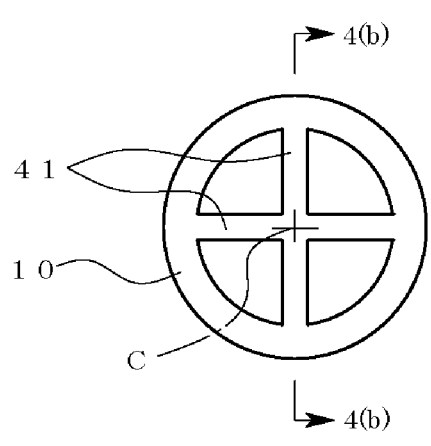
FIG. 4(a) is an enlarged front view according to a fourth embodiment of the crushing tip of the present invention.
Figure 4B:
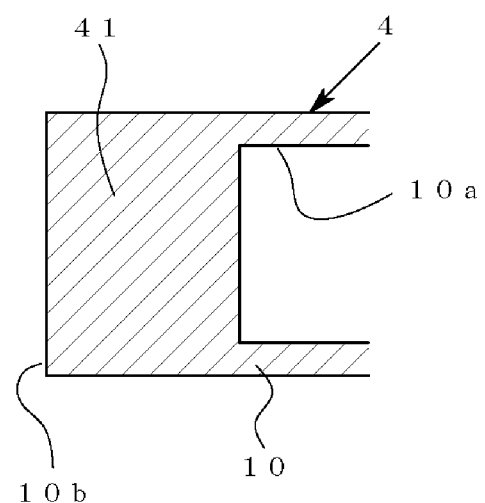
FIG. 4(b) is a cross-sectional view taken along a line 4(b)-4(b) in FIG. 4(a).

FIG. 4(a) is an enlarged front view according to a fourth embodiment of the crushing tip of the present invention, and FIG. 4(b) is a cross-sectional view taken along a line 4(b)-4(b) in FIG. 4(a).

In a crushing tip 4 of the embodiment, two partition walls 41 and 41 crossing each other are provided inside the through hole 10a. As shown in FIG. 4(a), the respective two partition walls 41 and 41 are provided inside the through hole 10a in such a way as to cross the through hole 10a passing the rotational center C of the crushing tip 4, and as shown in FIG. 4(b), one end thereof (left end in FIG. 4(b)) is positioned inside the same face as the tip face 10b of the tip main member 10.

Fifth Embodiment

Figure 5A:
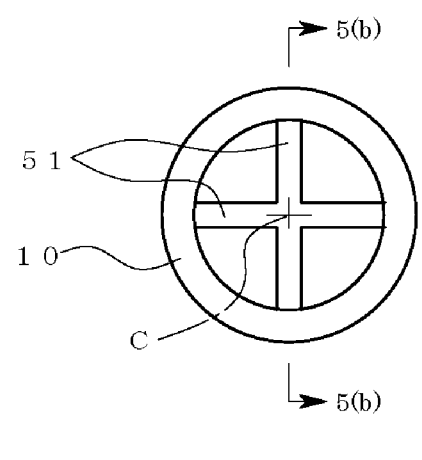
FIG. 5(a) is an enlarged front view according to a fifth embodiment of the crushing tip of the present invention.
Figure 5B:
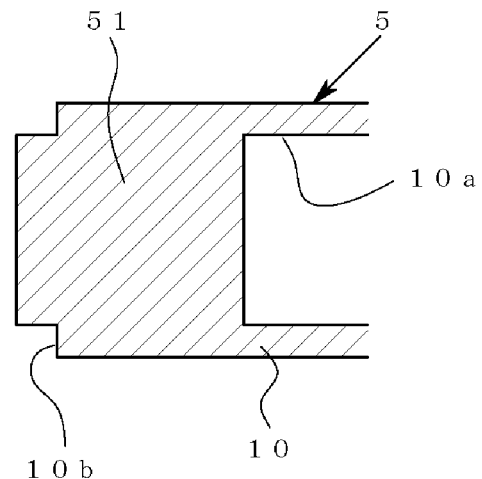
FIG. 5(b) is a cross-sectional view taken along a line 5(b)-5(b) in FIG. 5(a).

FIG. 5(a) is an enlarged front view according to a fifth embodiment of the crushing tip of the present invention, and FIG. 5(b) is a cross-sectional view taken along a line 5(b)-5(b) in FIG. 5(a).

A crushing tip 5 of the embodiment differs from the crushing tip 4 of the fourth embodiment in that as shown in FIG. 5(b), respective ends (left end in FIG. 5(b)) of partition walls 51 and 51 crossing each other project with the same width as the partition walls 41 of the fourth embodiment from the tip face 10b of the tip main member 10.

Sixth Embodiment

Figure 6A:
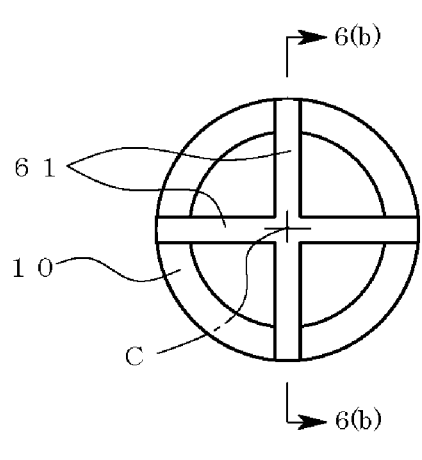
FIG. 6(a) is an enlarged front view according to a sixth embodiment of the crushing tip of the present invention.
Figure 6B:
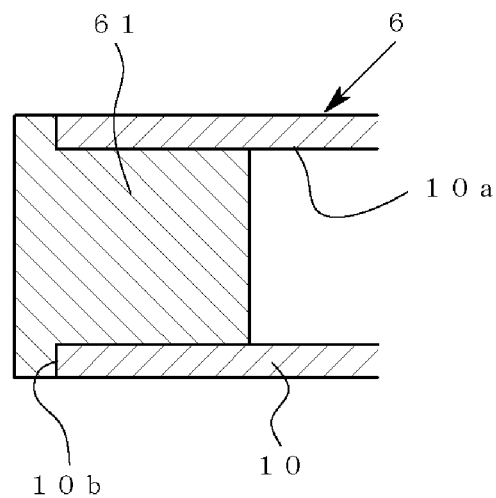
FIG. 6(b) is a cross-sectional view taken along a line 6(b)-6(b) in FIG. 6(a).

FIG. 6(a) is an enlarged front view according to a sixth embodiment of the crushing tip of the present invention, and FIG. 6(b) is a cross-sectional view taken along a line 6(b)-6(b) in FIG. 6(a).

A crushing tip 6 of the embodiment differs from the crushing tip 5 of the fifth embodiment in that as shown in FIGS. 6(a) and 6(b), respective ends (left end in FIG. 6(b)) of partition walls 61 and 61 projecting from the tip face 10b of the tip main member 10 extend to the outer peripheral edge of the tip main member 10 in the width direction in FIG. 6(a).

Seventh Embodiment

FIG. 7(a) is an enlarged front view according to a seventh embodiment of the crushing tip of the present invention, and FIG. 7(b) is a cross-sectional view taken along a line 7( )-7(b) in FIG. 7(a).

In a crushing tip 7 of the embodiment, two partition walls 71 and 71 disposed in parallel are provided inside the through hole 10a. As shown in FIG. 7(a), the respective two partition walls 71 and 71 are provided in such a way as to cross the through hole 10a at a position off-center from the rotational center C of the crushing tip 7, and as shown in FIG. 7(b), one end thereof (left end in FIG. 7(b)) is positioned inside the same face as the tip face 10b of the tip main member 10.

Eighth Embodiment

FIG. 8(a) is an enlarged front view according to an eighth embodiment of the crushing tip of the present invention, and FIG. 8(b) is a cross-sectional view taken along a line 8(b)-8(b) in FIG. 8(a).

A crushing tip 8 of the embodiment differs from the crushing tip 7 of the seventh embodiment in that as shown in FIG. 8(b), respective ends (left ends in FIG. 8(b)) of the parallel partition walls 71 and 71 project from the tip face 10b of the tip main member 10 with the same width as the partition walls 71 and 71 of the seventh embodiment.

Ninth Embodiment

FIG. 9(a) is an enlarged front view according to a ninth embodiment of the crushing tip of the present invention, and FIG. 9(b) is a cross-sectional view taken along a line 9(b)-9(b) in FIG. 9(a).

A crushing tip 9 of the embodiment differs from the crushing tip 8 of the eighth embodiment in that as shown in FIGS. 9(a) and 9(b), respective ends (left ends in FIG. 9(b)) of partition walls 91 and 91 projecting from the tip face 10b of the tip main member 10 extend to the outer peripheral edge of the tip main member 10 in the width direction in FIG. 9(a).

Tenth Embodiment

FIG. 10(a) is an enlarged front view according to a tenth embodiment of the crushing tip of the present invention, and FIG. 10(b) is a cross-sectional view taken along a line 10(b)-10(b) in FIG. 10(a).

A crushing tip 100 of the embodiment is a modified example of the eighth embodiment shown in FIGS. 8(a) and 8(b), and differs from the eighth embodiment in that another partition wall 102 is provided in such a way as to intersect parallel partition walls 101 and 101 which are the same as the partition walls in FIGS. 8(a) and 8(b). A plurality of partition walls 102 may be provided as well.

Incidentally, although it is not specially shown in the drawings, one or a plurality of partition walls same as the partition wall 102 may be provided in such a way as to intersect the partition walls 91 of the ninth embodiment shown in FIGS. 9(a) and 9(b).

Eleventh Embodiment

Figure 11A:
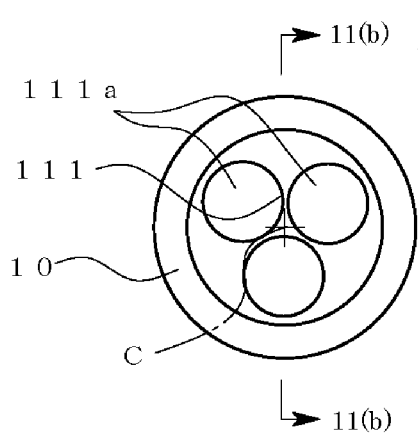
FIG. 11(a) is an enlarged front view according to an eleventh embodiment of the crushing tip of the present invention.
Figure 11B:
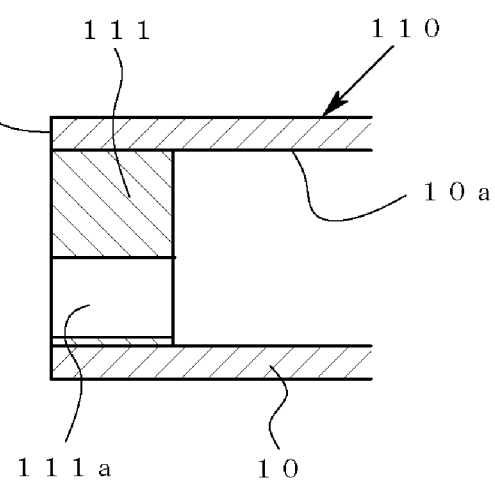
FIG. 11(b) is a cross-sectional view taken along a line 11(b)-11(b) in FIG. 11(a).

FIG. 11(a) is an enlarged front view according to an eleventh embodiment of the crushing tip of the present invention, and FIG. 11(b) is a cross-sectional view taken along a line 11(b)-11(b) in FIG. 11(a).

In a crushing tip 110 of the embodiment, a partition wall 111 is formed between holes 111a and 111a by a plurality of circular holes 111a bored at a tip of the tip main member 10. According to the embodiment, for example, a block is fitted into the tip of the tip main member 10, and the circular or oval hole 111a is pierced and formed in the block with a drill, or by an electric discharge machining and the like so as to form the partition wall 111. In the illustrated example, three holes 111a are formed, however, two, or four or more holes 111a may be formed.

Other Embodiments

FIGS. 12(a), 12(b), and 12(c), and FIGS. 13(a), 13(b), and 13(c) are enlarged front views of the crushing tip according to other embodiments of the present invention.

In the crushing tips 1 to 9, 100, and 110 shown in FIG. 1(a) to FIG. 11(b), at least the portion to be inserted into the crystalline lens in the tip main member 10 has the circular shape in cross section, however, in crushing tips 120 and 130 of the other embodiments shown in FIGS. 12(a) to FIG. 13(c), a cross-sectional shape is an oval shape (in examples shown in FIG. 12(a) to FIG. 13(c), a rectangle with rounded corners).

Figure 12A:
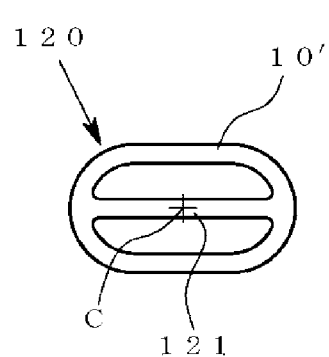
FIGS. 12(a), 12(b), and 12(c) are enlarged front views according to another embodiment of the crushing tip of the present invention.
Figure 12B:
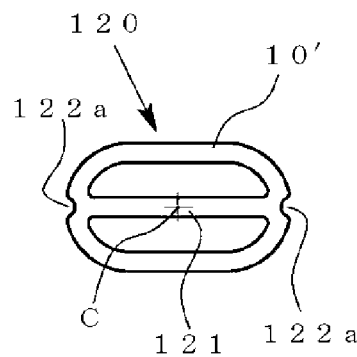
Figure 12C:
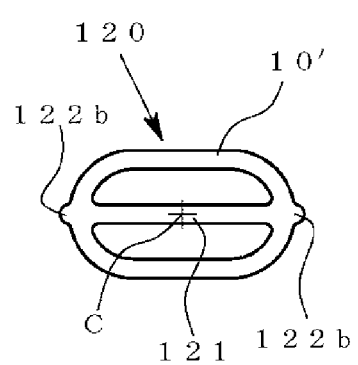

In the crushing tip 120 shown in FIGS. 12(a) to 12(c), a partition wall 121 is provided inside a through hole 10a' of a tip main member 10'. The embodiment of the partition wall 121 in the crushing tip 120 shown in FIGS. 12(a) to 12(c) can be the embodiment same as the partition walls 11 to 31 of the crushing tips 1 to 3 shown in the embodiments of FIG. 1(a) to FIG. 3(b). Also, although it is not shown in the drawings, still another partition wall can be provided in a direction of intersecting the partition wall 121 so as to have the embodiment same as the partition walls 41 to 61 of the crushing tips 4 to 6 shown in FIG. 4(a) to FIG. 6(b). Furthermore, although it is not shown in the drawings, a plurality of partition walls 121 can be provided in parallel so as to have the embodiment same as the partition walls 71 to 91 of the crushing tips 7 to 9 shown in FIG. 7(a) to FIG. 9(b). Furthermore, one or a plurality of partition walls is provided in a direction of intersecting the partition wall 121 so as to have the embodiment same as the partition walls 101 of the crushing tip 100 shown in FIGS. 10(a) and 10(b).

Also, the crushing tip 130 shown in FIGS. 13(a), 13(b), and 13(c) includes a plurality of circular holes 121a bored at a tip of the tip main member 10', and a partition wall is formed between the holes 121a and 121a in the same manner as the crushing tip 110 in FIGS. 11(a) and 11(b). Even in the crushing tip 130, the number of the holes 121a may be two, or four or more.

Furthermore, in the crushing tips 120 and 130 in FIG. 12(a) to FIG. 13(c), as shown in FIG. 12(b) and FIG. 13(b), concave portions 122a may be formed at a tip of a semicircle portion formed on both ends of the tip main member 10', or as shown in FIG. 12(c) and FIG. 13(c), convex portions 122b may be formed at the tip of the semicircle portion of the tip main member 10'.

Figure 15A:
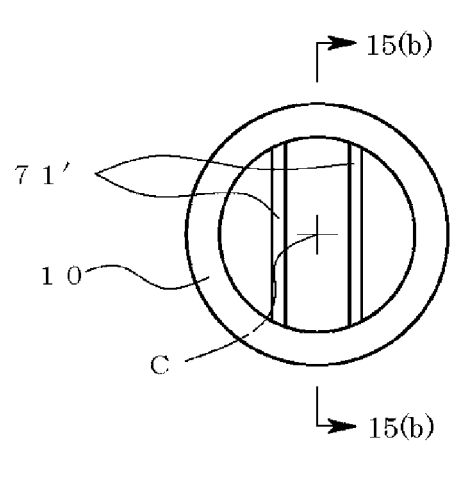
FIG. 15(a) is an enlarged front view according to still another embodiment of the crushing tip of the present invention.
Figure 15B:
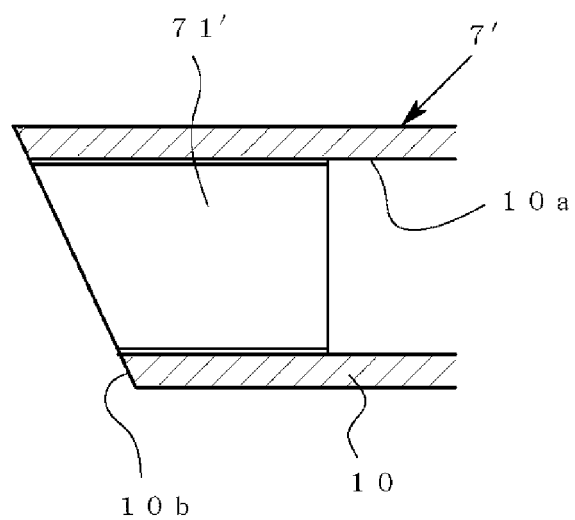
FIG. 15(b) is a cross-sectional view taken along a line 15(b)-15(b) in FIG. 15(a).

Also, the tip of the crushing tips 1 to 9, 100, 110, 120, and 130 of the aforementioned embodiments may be obliquely cut and sharpened. For example, a crushing tip 4' shown in FIGS. 14(a) and 14(b) is based on the crushing tip 4 shown in FIGS. 4(a) and 4(b), and the tip face 10b of the tip main member 10 and a partition wall 41' have a shape obliquely cut. Also, a crushing tip 7' shown in FIGS. 15(a) and 15(b) is based on the crushing tip 7 shown in FIGS. 7(a) and 7(b), and the tip face 10b of the tip main member 10 and a partition wall 71' have a shape obliquely cut.

In the crushing tips 1 to 10, 100, 110, 120, and 130 of the aforementioned first to eleventh embodiments, and the other embodiments, in view of an inhibiting effect of the occurrence of the cavitation, a crushing and emulsifying efficiency, and the like, there is selected any of a traditional mode allowing the crushing tips 1 to 10, 100, 110, 120, and 130 to have reciprocating vibrations in a axial line direction of the rotational center C, or a torsional mode allowing the crushing tips 1 to 10, 100, 110, 120, and 130 to have repetitive rotational vibrations around the rotational center C so as to provide the ultrasonic vibrations. As for a frequency of the provided ultrasonic vibrations, a frequency usually used for a similar type of surgeries can be used, and in the traditional mode, the frequency is approximately from 32 kHz to 40 kHz, and in the torsional mode, the frequency is approximately from 38 kHz to 40 kHz.

In the present invention, a contact area between the crystalline lens and the crushing tips 1 to 10, 100, 110, 120, and 130 increases by the partition walls 11 to 111, and 121 so as to increase a crushing effect of the crystalline lens by the ultrasonic vibrations compared to conventional crushing tips, and efficiently crush, suck, and discharge the crystalline lens.

The partition walls 11 to 111, and 121 are formed in such a way as to cross the through holes 10a and 10a' so as to be difficult to generate the cavitation. Even if the cavitation occurs, an amount thereof is small compared to the conventional crushing tips, and the cavitation occurs inside the through holes 10a and 10a', or near the tip face 10b of the tip main members 10 and 10', so that the cavitation is sucked simultaneously when it occurs by suction simultaneously carried out with crushing of the crystalline lens, and the cavitation is hardly released to the outside of the crushing tips 1 to 10, 100, 110, 120, and 130.

Thus, in the present invention, the crystalline lens can be efficiently crushed, sucked, and discharged while effectively restraining the cavitation from occurring.

The preferred embodiments of the present invention have been explained, however, the present invention is not limited to the aforementioned explanation.

For example, in the fourth to sixth embodiments, the respective partition walls 41, 51, and 61 are crossed perpendicularly, however, an intersecting angle is not limited to a right angle. Also, in the fourth to tenth embodiments, three or more partition walls 41, 51, and 61 may be intersected, or three or more partition walls 71, 81, 91, 101, and 102 may be disposed in parallel. Moreover, one, or two or more partition walls may be intersected and disposed in the partition walls 71, 81, 91, 101, and 102 disposed in parallel.

INDUSTRIAL APPLICABILITY

The crushing tip of the present invention can be extensively applied to surgeries which require the crystalline lens to be crushed and taken out, and especially, can be preferably applied to a surgery for cataract treatment.

The disclosure of Japanese Patent Application No. 2016-146845, filed on Jul. 27, 2016 is incorporated in the application.

While the invention has been explained with reference to the specific embodiments of the invention, the explanation is illustrative and the invention is limited only by the appended claims.

What is claimed is:

1. A crushing tip for an eye surgery, which is adapted to be inserted into a crystalline lens of an eye of a patient at a time of an eye surgery for crushing, sucking, and discharging the crystalline lens by providing ultrasonic vibrations, comprising:
   a cylindrical tip main member having a tip end face at one end, and a through hole; and
   a partition wall having one end and provided in the through hole to cross therethrough,
   wherein the one end of the partition wall is positioned on a same face as the tip end face at the one end of the tip main member.

2. A crushing tip for an eye surgery according to claim 1, wherein the tip main member is formed in a straight shape in a transmitting axial line direction of the ultrasonic vibrations.

3. A crushing tip for an eye surgery according to claim 1, wherein at least a portion of the tip main member, which is adapted to be inserted into the crystalline lens, is formed in a circular shape or an oval shape in cross section.

4. A crushing tip for an eye surgery according to claim 1, wherein the partition wall is integrally formed with the tip main member as one member.

5. A crushing tip for an eye surgery according to claim 4, wherein a depth of the partition wall is substantially same as an outer diameter of the tip main body.

6. A crushing tip for an eye surgery according to claim 1, wherein the partition wall is arranged to pass a rotational center of the crushing tip.

7. A crushing tip for an eye surgery according to claim 1, wherein the tip end face of the tip main member and the one end of the partition wall have a shape obliquely cut.

* * * * *